United States Patent
Raja et al.

(10) Patent No.: US 11,851,400 B2
(45) Date of Patent: Dec. 26, 2023

(54) INTENSIFIED PROCESS OF SYNTHESIS OF DIALKYL ETHERS USING A STEP CONICAL REACTOR

(71) Applicant: Council of Scientific and Industrial Research, New Delhi (IN)

(72) Inventors: Thirumalaiswamy Raja, Pune (IN); Vipul Subhash Patil, Pune (IN); Siva Prasad Mekla, Pune (IN); Snehal Narayan Teli, Pune (IN); Kiran Chandrashekhar Chavhan, Pune (IN); Akash Ravindra Bhatkar, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 17/614,965

(22) PCT Filed: May 27, 2020

(86) PCT No.: PCT/IN2020/050476
§ 371 (c)(1),
(2) Date: Nov. 29, 2021

(87) PCT Pub. No.: WO2020/240591
PCT Pub. Date: Dec. 3, 2020

(65) Prior Publication Data
US 2022/0234978 A1    Jul. 28, 2022

(30) Foreign Application Priority Data
May 27, 2019 (IN) .............................. 201911020867

(51) Int. Cl.
*C07C 41/09* (2006.01)
*B01D 3/34* (2006.01)
(Continued)

(52) U.S. Cl.
CPC .............. *C07C 41/09* (2013.01); *B01D 3/009* (2013.01); *B01D 3/346* (2013.01); *C07C 41/42* (2013.01)

(58) Field of Classification Search
CPC ........ B01D 3/009; B01D 3/346; C07C 41/09; C07C 41/42
See application file for complete search history.

(56) References Cited

U.S. PATENT DOCUMENTS 4,732,784 A * 3/1988 Laroche ..................... C10J 3/20
                                                    427/230
5,037,511 A * 8/1991 Dornhagen ............. C07C 41/42
                                                    203/99
(Continued)

FOREIGN PATENT DOCUMENTS

CN            1907932 A         2/2007
CN          101386569 A         3/2009
(Continued)

OTHER PUBLICATIONS

Lei et al. ("Synthesis of dimethyl ether (DME) by catalytic distillation", Chemical Engineering Science, vol. 66, Issue 14, Jul. 2011, pp. 3195-3203). (Year: 2011).*

(Continued)

*Primary Examiner* — Jonathan Miller
(74) *Attorney, Agent, or Firm* — Blank Rome LLP

(57) ABSTRACT

The present invention relates to an intensification of the synthetic process for the preparation of dialkyl ether from alcohol by using a conical fixed bed reactor integrated with distillation coupled conical polishing reactor.

12 Claims, 9 Drawing Sheets

(51) Int. Cl.
*B01D 3/00* (2006.01)
*C07C 41/42* (2006.01)

(56) References Cited

U.S. PATENT DOCUMENTS

| | | | | | |
|---|---|---|---|---|---|
| 5,221,441 | A | * | 6/1993 | Smith, Jr. | B01D 3/009 585/446 |
| 5,248,836 | A | * | 9/1993 | Bakshi | C07C 41/06 568/697 |
| 6,723,886 | B2 | * | 4/2004 | Allison | C07C 1/041 568/876 |
| 8,350,095 | B2 | * | 1/2013 | Varkiani | C07C 41/42 568/699 |
| 2009/0048468 | A1 | * | 2/2009 | Varkiani | C07C 41/42 568/671 |
| 2009/0069607 | A1 | | 3/2009 | Smith, Jr. et al. | |
| 2013/0211147 | A1 | | 8/2013 | Cheiky et al. | |
| 2016/0030856 | A1 | * | 2/2016 | Kaplan | B01D 39/2027 422/187 |
| 2022/0234978 | A1 | * | 7/2022 | Raja | B01D 3/009 |

FOREIGN PATENT DOCUMENTS

| | | |
|---|---|---|
| CN | 101434518 A | 5/2009 |
| CN | 105367457 A | 3/2016 |
| EP | 0407038 A1 | 1/1991 |
| EP | 0485078 A1 | 5/1992 |

OTHER PUBLICATIONS

Indian First Examination Report for IN 201911020867, dated Jun. 22, 2022, 5 pgs.
Chinese Office Action and Translation for CN 2020800480197, dated Mar. 31, 2023,16 pgs.
International Search Report & Written Opinion for PCT/IN2020/050476, dated Sep. 7, 2020, 8 pgs.
Z. Bai, et al., "Process Simulation of Dimethyl Ether Synthesis via Methanol Vapor Phase Dehydration", Polish Journal of Chemical Technology; vol. 15, No. 2, 2013, pp. 122-127.
M. Fazlollahnejad, et al., "Experimental Study and Modeling of an Adiabatic Fixed-bed Reactor for Methanol Dehydration to Dimethyl Ether", Catalysis, Kinetics and Reactors, Chinese Journal of Chemical Engineering, vol. 17, No. 4, 2009, pp. 630-634.

* cited by examiner

INTENSIFIED PROCESS OF SYNTHESIS OF DIALKYL ETHERS USING A STEP CONICAL REACTOR

RELATED APPLICATIONS

This application is a national phase application of International Application No. PCT/IN2020/0504176, filed May 27, 2020, which claims the benefit of Indian Patent Application No. 201911020867, filed on May 27, 2019. The entire contents of these applications are hereby incorporated by reference.

FIELD OF THE INVENTION

The present invention relates to an intensification of the synthesis of dialkyl ether using a new process including a step conical fixed bed reactor coupled with polishing reactive distillation unit. Particularly, the present invention relates to an intensification of the synthetic process of dimethyl ether from methanol dehydration by using a conical fixed bed reactor integrated with distillation coupled conical polishing reactor.

BACKGROUND AND PRIOR ART OF THE INVENTION

Nowadays highly increasing air pollution calls for the need for clean alternative fuel. Recently, attempts are going on to replace chlorofluorocarbons (CFC) with effective chemicals and aerosol propellants. The main raw material used for the synthesis of these chemicals and aerosol propellants is dialkyl ethers, and more particularly dimethyl ether (DME), which has received attention as a LPG alternative for transportation fuel instead of diesel and power generation.

For the synthesis of large scale basic chemicals and intermediates, catalytic fixed-bed reactors are the most important type of reactor. It is mainly used for heterogeneously catalyzed gas reactions that take place on the surface of the catalyst which is arranged as a so-called fixed bed in these reactors. Heterogeneous catalytic reactors emphasizecatalyst effectiveness factors and the heat and mass transfer implications. In a fixed bed reactor, the cylindrical tube of the reactor is filled with reactants along with catalysts, which are being flowed through the reactor bed and converted into the desired product. The catalyst may have multiple configurations including one large bed, several horizontal beds, several parallel packed tubes, and multiple beds in their own shells. Depending on the need to maintain temperature control within the system, various configurations may be adapted.

The process for the conversion of methanol into dimethyl ether is an equilibrium constraint reaction, highly exothermic reaction so heat should be taken out of the catalytic bed otherwise it may lead to the formation of hot spots and this may result into the thermal cracking of the products as well as deactivation of the active reactants and it may shift the reaction equilibrium towards reactant side as heat is one of the products of the reaction. Methanol dehydration to give dimethyl ether has thermodynamic limitations which restrict the conversion of the reaction. Few efforts are made to synthesize dimethyl ether from methanol by designing the reactor for the reaction in the art.

The article titled "Experimental Study and Modeling of an Adiabatic Fixed-bed Reactor for Methanol Dehydration to Dimethyl Ether" by M. Fazlollahnejadl, M. Taghizadehl et. al and published in the journal "*Chinese Journal of Chemical Engineering,* 17(4), 630-634, (2009)" reports One-dimensional heterogeneous plug flow adiabatic fixed-bed reactor for the catalytic dehydration of methanol to dimethyl ether. The reactor is packed with 1.5 mm —Al2O3 pellets as a dehydration catalyst and operated in a temperature range of 543-603 K at atmospheric pressure.

US patent application US2013/0211147A1 published on 15 Aug. 2013 discloses a heterogeneous catalyst that allows efficient syngas conversion to dimethyl ether at lower pressures.

The article titled "Process simulation of dimethyl ether synthesis via methanol vapour phase dehydration" by Weiyong Ying et. al and published in the journal "*Pol. J. Chem. Tech.*, Vol. 15, No. 2, 2013" reports production process of catalytic dehydration of methanol in an adiabatic fixed-bed reactor and two columns product separations. The technological process for dimethyl ether (DME) synthesis is built on the PRO/II platform based on the combined parameters of the reaction dynamic model for methanol dehydration reaction, the improved NRTL model of the liquid phase, the PR model of the vapour phase.

There is a need in the art to solve the problems associated with selectivity, heat dissipation, cracking, coke formation and catalyst deactivation and reaction equilibrium, high superficial velocity of fluids by designing an appropriate fixed bed reactor. In conventional fixed bed reactors, it may be difficult to control heat dissipation properly which may lead to low selectivity and catalyst deactivation.

There is a need to design new process with modified fixed bed reactor coupled with—post-processing and polishing unit for the process of dimethyl ether synthesis by dehydration of methanol, which may provide an increase in the catalyst activity, higher conversion, selectivity, catalyst life, and in-situ heat and product removal which can save the cost of post-processing of the product.

OBJECTS OF THE INVENTION

The main objective of the present invention is to provide an intensified process for the preparation of dialkyl ethers by using a step conical fixed bed reactor coupled with polishing reactive distillation unit.

Another objective of the present invention is to provide fixed bed reactor of a conical shape with an increasing diameter of the reactor with other parts such as the condenser, phase separator, distillation column, and polishing reactor, and so on to obtain an intensified process for the preparation of dialkyl ethers.

ACRONYMS USED TO DESCRIBE THE INVENTION

BPR: Back Pressure Regulator
FBR: Fix bed reactor
WHSV: weight hourly space velocity
DME: Dimethyl ether
GC: Gas chromatography
HPLC: High-Performance Liquid Chromatography
DEE: Di ethyl ether

SUMMARY OF THE INVENTION

Accordingly, present invention provides an intensified process for the preparation of dialkyl ether comprising the step of:

dehydrating alcohol in a step conical fixed bed reactor coupled with a polishing reactive distillation unit by injecting a liquid alcohol, at a flow rate of 2.65-8.5 ml·min$^{-1}$ and WHSV of 0.5-1.6 h$^{-1}$ at temperature in the range of 200-260° C. under 1-10 bar pressure at reactor system to obtain dialkyl ether, wherein said process is catalyst independent.

In an embodiment of the present invention, said dialkyl ether is dimethyl or diethyl ether.

In an embodiment, present invention provides a step conical fixed bed reactor comprising:
 i. Heat Exchanger (FIG. 1, 2);
 ii. Phase Separator—1 (FIG. 1, 3);
 iii. Reactive Distillation Column (FIG. 1, 4);
 iv. Liquid Collector (FIG. 1, 5);
 v. Phase Separator—2 (FIG. 1, 6);
 vi. Demister pad (FIG. 1, 7);
 vii. Perforated screen for catalyst support (FIG. 1, 8);
 viii. Polishing Catalyst (FIG. 1, 9);
 ix. Back Pressure Regulator (BPR) (FIG. 1, 10);
 x. Level Control Indicator (LCR) (FIG. 1, 11) and;
 xi. Reflux Inlet (FIG. 1, 12).

In yet another embodiment of the present invention, conical fixed bed reactor further comprising:
 i. inlet for reactant (FIG. 2, 1");
 ii. cooling water outlet (FIG. 2, 2");
 iii. cooling water inlet (FIG. 2,3").

In yet another embodiment of the present invention, said step conical fixed bed reactor involves multiple feed entries for multiple reactions.

In yet another embodiment of the present invention, said reactor is equipped with in-situ heat integration and cooling arrangements.

In yet another embodiment of the present invention, said reactor provides 5-100 micron size of a catalyst support mesh to get desirable back pressure to avoid channeling.

In yet another embodiment of the present invention, said reactor is equipped with an inner diameter gradually increasing per step from 3.3×x cm, 5.3×x cm and 7.3×x cm, respectively, wherein x is scaling factor which depends on the amount of catalyst loaded in the reactor and the step conical arrangement of said reactor is a steep angle of 10-90°.

In yet another embodiment of the present invention, said reactor gives 30-50% higher reaction throughput.

In yet another embodiment of the present invention, said reactor is used for the synthesis of dialkyl ethers.

BRIEF DESCRIPTION OF THE DRAWINGS

FIG. 2 shows the Stepwise Conical reactor design wherein (1) is Methanol inlet; (2") Cooling water out and (3") is Cooling water in.

DETAILED DESCRIPTION OF THE INVENTION

The present invention provides an intensified process for the preparation of dialkyl ethers by using a step conical fixed bed reactor coupled with a polishing reactive distillation unit. More particularly, intensification of the process for the synthesis of dimethyl ether by dehydration of methanol, wherein the throughput of the process is at least 30-50% improved in comparison to the process in a conventional reactor, independent of catalyst.

In the invention, a conical fixed bed reactor coupled with a polishing reactive distillation unit is set for highly temperature-dependent, exothermic synthesis of dimethyl ether by dehydration of methanol in the presence of a dehydrating agent. In-situ product separation, heat, and pressure integration by using conical fixed bed separator solve the problems associated with equilibrium constrain and can push the reaction equilibrium towards the product side. The conventional reactor process is associated with problems like selectivity, heat dissipation, cracking, coke formation and catalyst deactivation, high superficial velocity of fluids which are solved with a new set up of the conical fixed bed reactor.

Figure 1:
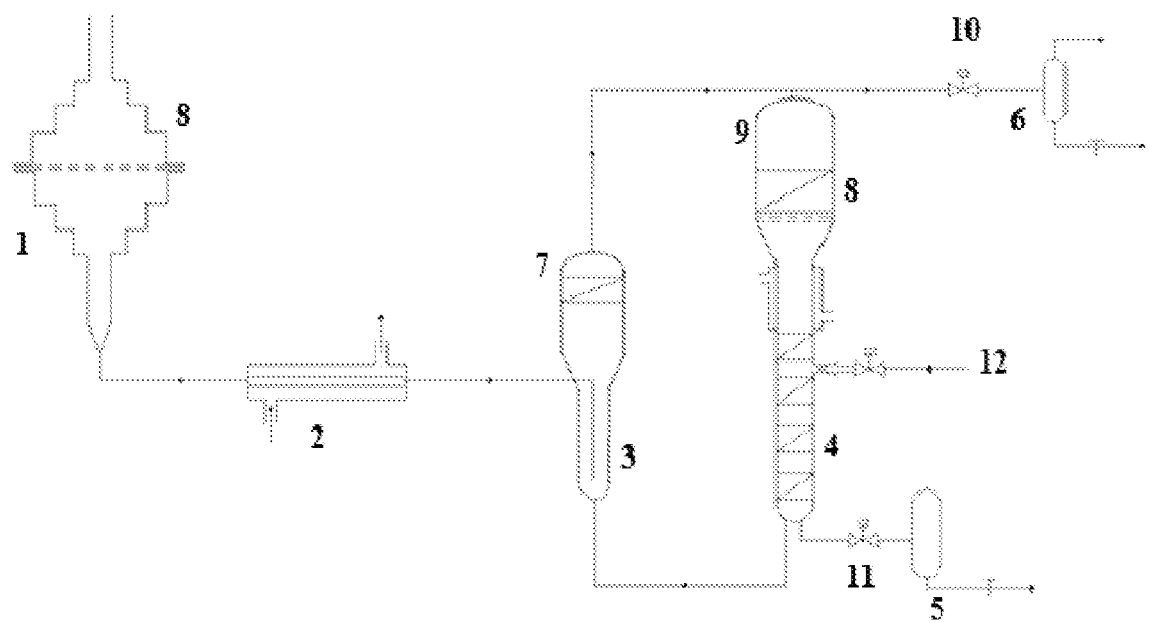
FIG. 1 depicts the reactor design wherein (1) is Reactor, (2) is Heat Exchanger, (3) Phase Separator—1, (4) is Reactive Distillation Column; (5) is Liquid Collector; (6) Phase Separator—2, (7) is Demister pad; (8) is Perforated screen for catalyst support; (9) is Polishing Catalyst; (10) is Back Pressure Regulator (BPR); (11) is Level Control Indicator (LCR) and (12) is Reflux Inlet.

Present invention provides a fixed bed reactor of a conical shape with an increasing diameter of the reactor along with other parts such as the condenser, phase separator, distillation column, and polishing reactor, and so on as shown in FIG. 1.

An intensified process for the preparation of dialkyl ethers comprises of dehydrating alcohol in a step conical fixed bed reactor coupled with polishing reactive distillation unit by injecting a liquid alcohol, at a flow rate of 2.65-8.5 ml·min$^{-1}$ and WHSV of 0.5-1.6 h$^{-1}$ at a temperature in the range of 250-260° C. under 1-10 bar pressure at reactor system.

In an embodiment of the present invention, said dialkyl ether is dimethyl or diethyl ether.

Process for the preparation of dimethyl ether involves dehydration of methanol in the presence of dehydrating agents such as Glycols like s ethylene glycol (EG), diethylene glycol (DEG), triethylene glycol (TEG), and tetraethylene glycol (T4EG) and Sulfuric acid, concentrated phosphoric acid for catalytic activity and is associated with problems like selectivity, heat dissipation, cracking, coke formation, and catalyst deactivation. In-situ product separation, heat, and pressure integration by using newly designed conical fixed bed separators solve the problems associated with equilibrium constrain and can push the reaction equilibrium towards the product side. It can also enhance the catalyst life by avoiding cracking.

When the catalyst is loaded in a fixed bed reactor, then the reaction occurs at the initial layer of the catalyst. Water is formed during the reaction, which affects the layers beneath of the catalyst making them unused as water is competing with the methanol to adsorb on the active sites of the catalyst. Water is restricting the adsorption of the incoming fresh lot of methanol on catalyst surface to react and thus making the output of the process poor by diluting incoming reactant methanol.

Thus, in the particularly preferred embodiment, a process for the preparation of dialkyl ether, particularly, dimethyl and diethyl ether is intensified by using a fixed bed reactor of a conical shape with stepwise increasing diameter of the reactor with a step angle of 10-90-depending on the reactant/product properties as shown in FIG. 1.

In an embodiment, present invention provides a step conical fixed bed reactor comprising:
- xii. Heat Exchanger (FIG. 1, 2);
- xiii. Phase Separator—1 (FIG. 1, 3);
- xiv. Reactive Distillation Column (FIG. 1, 4);
- xv. Liquid Collector (FIG. 1, 5);
- xvi. Phase Separator—2 (FIG. 1, 6);
- xvii. Demister pad (FIG. 1, 7);
- xviii. Perforated screen for catalyst support (FIG. 1, 8);
- xix. Polishing Catalyst (FIG. 1, 9);
- xx. Back Pressure Regulator (BPR) (FIG. 1, 10);
- xxi. Level Control Indicator (LCR) (FIG. 1, 11) and;
- xxii. Reflux Inlet (FIG. 1, 12).

Figure 2:
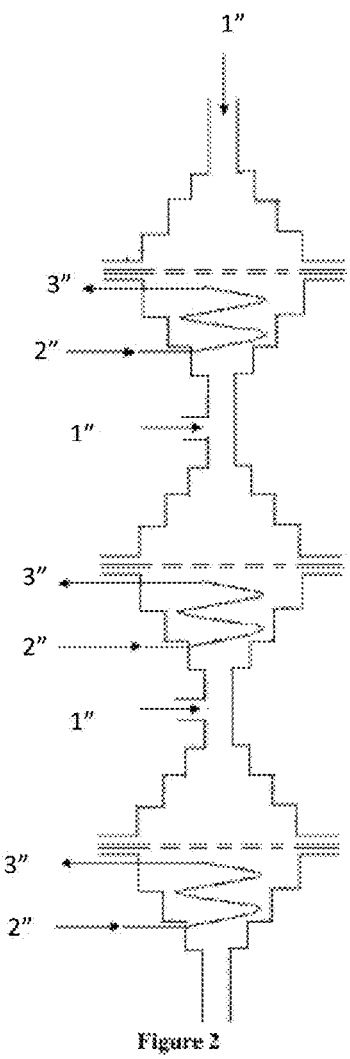

In yet another embodiment of the present invention, conical fixed bed reactor further comprising:
- iv. inlet for reactant (FIG. 2, 1");
- v. cooling water outlet (FIG. 2, 2");
- vi. cooling water inlet (FIG. 2,3").

In yet another embodiment of the present invention, said step conical fixed bed reactor involves multiple feed entries for multiple reactions.

In yet another embodiment of the present invention, said reactor is equipped with in-situ heat integration and cooling arrangements.

In another embodiment of the present invention, reactor set up for the preparation of dialkyl ether to intensify the process is provided consisting of a conical fixed bed reactor with the inner diameter gradually increasing per step from 1.3×x, 3.3×x cm, 5.3×x cm and 7.3×x cm respectively where x is scaling factor which depends on the amount of catalyst loading in the reactor. The step conical reactor facilitates to vary the steps diameter of the reactor which helps to maintain the superficial velocity inside the reactor and steep angle of 10-90° depends on the type of reaction and nature of reactants and product results in static pressure recovery, proper heat distribution over catalyst bed, entrainment mass flux rates and maximize the throughput of the reaction. Step conical reactor which exemplified here offers reactor diameters ranging from 1.3 cm (catalyst bed inlet) to 7.3 cm (catalyst bed exit) which offers a maximum surface of catalyst for fresh incoming of feed and helps to avoid hot spots in the catalyst bed. The reactor can provide multiple feed entries improving the flexibility of using multiple reactants into the reactor. Multiple feed entries and cooling coils facilitate the in situ cooling of product gas which helps to avoid hotspot and cracking on catalyst surface resulting in the increase in catalyst life. Size of mesh is 5-100 micron is provided to give required back pressure to support catalyst which avoids channeling of the reactants. In an embodiment, the step conical fixed bed reactor has a provision for giving cold shots or quenching arrangements to avoid the hot spot formation.

In another embodiment of the present invention, the process offers a new set up of the reactor which helps to improve the yield of the dehydration/exothermic reactions. Step conical reactor is further connected with a phase separator where dimethyl ether is removed from the ternary reactor outlet stream by keeping the temperature appropriate at the bottom of the phase separator using an intermediate cooler. The liquid, which remains at the bottom of the phase separator mainly, contains unreacted reactant (methanol) and by-product (water), which is further distilled in the reboiler of the reactive distillation column here and methanol is separated out in vapor phase and further purified in rectifying section by refluxing fresh methanol. The methanol vapors further travel into polishing catalyst zone without condensing them where they are further reacted to form dimethyl ether and water that saves energy for condensing, recycling and again evaporating the methanol. The chemical process of the present invention by using the new reactor set up offers some unique features such as in-situ separation of products, higher yields, high throughput of the process, and heat integration with energy and cost savings.

In yet another embodiment of the present invention, said reactor is used for the synthesis of dialkyl ethers.

A new conical fixed bed reactor set up gives by 30-50% higher throughput from the process for the preparation of dimethyl ether as the set up allows the fresh methanol to come in maximum contact with the catalyst and adsorbs on the maximum available surface area of the catalyst to increase dimethyl ether formation. Dimethyl ether is a gas with very low vapor density, which increases the super facial velocity of the fluids inflowing through the catalyst bed which minimizes the retention time of the reactant. Hence, the diameter of the reactor is increased in order to decrease the velocity. A new step by step conical shape fixed bed reactor set up also reduces the hot spots formed during exothermic reactions as it provides proper heat flux with the help of in-situ cooling coils. The reactor is further connected to phase separator operating at 10 bar follows the Distillative reactor and then condenser. The mixture of dimethyl ether vapours, water, and methanol is separated in-situ and unconverted methanol is passed over a bed of catalyst once again in a reactive distillation column to enhance the throughput.

Separation of dimethyl ether at a later stage gives better selectivity, purity, and a decrease in energy consumption. At the same time, methanol is also not condensed, which saves energy giving high conversions. The process is done at 260-265° C. in a reactor for the synthesis of dimethyl ether selectively, which is very low when compared to reported and known processes, and reaction temperature can be increased to 400-450° C. under atmospheric pressure for olefins synthesis.

Figure 3:
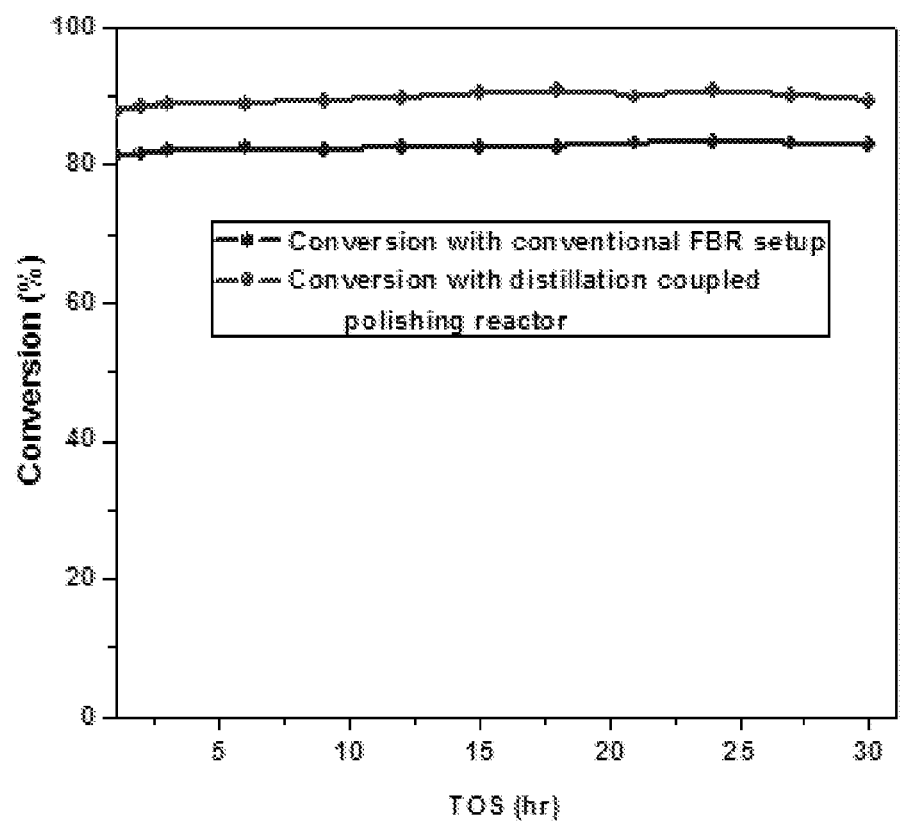
FIG. 3 shows conversion results comparison of conventional reactor versus distillation coupled reactor.

FIG. 1 depicts the reactor design diagram with the below numbers given to the different parts and FIG. 2 describes a conical reactor has a stepwise conical model with the numbers. A comparison of the conversion results of the conventional reactor versus the distillation coupled reactor is shown in FIG. 3. Performance plot shows that with conventional FBR (Fix bed reactor) conversion was around 80% at 10 bars and at 265° C. of reaction temperature with WHSV (weight hourly space velocity) whereas with distillation coupled polishing unit conversion reaches up to 88% with same reaction conditions.

Figure 4:
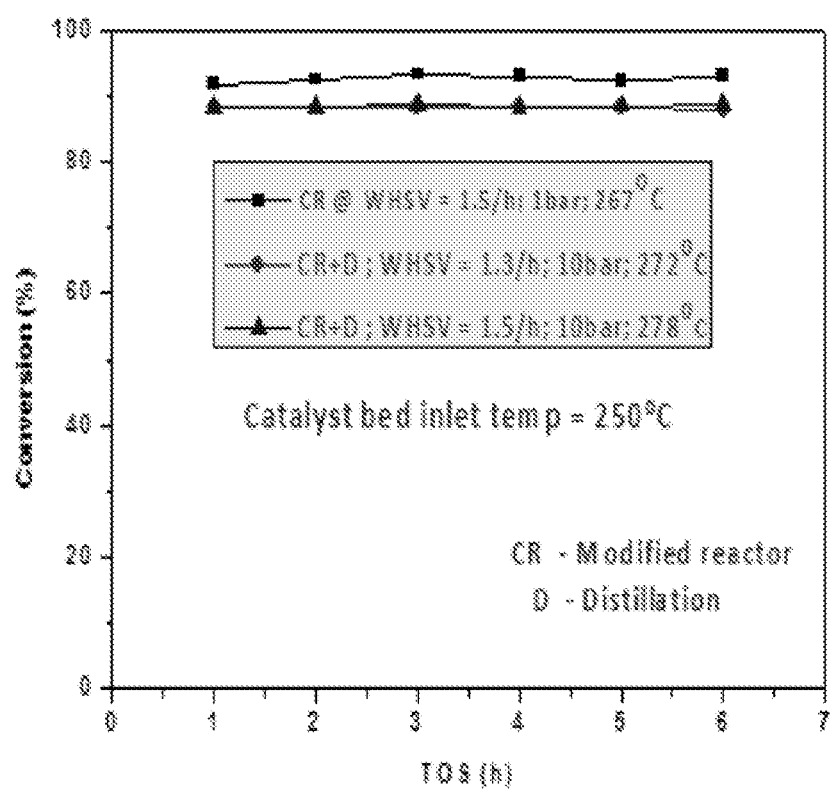
FIG. 4 depicts the comparison plot performance of the conical reactor at different reaction conditions.

The comparison plot performance of the conical reactor at different reaction conditions is shown in FIG. 4. Comparative plots show that the conversion of a conical reactor is around 88% at 1 bar with WHSV 1.5 at 267° C. whereas the same conversion is achieved at WHSV of 1.3 using a conventional fixed bed reactor. Results show that 15% reactor throughput is increased by reactor modifications. When this rector is further coupled with distillation coupled polishing reactor the same conversion can be achieved at 10 bar pressure whereas it is around 80% with a conventional reactor. These results show that around 30% reactor throughput is increased by reactor modifications at 10 bar.

Figure 5:
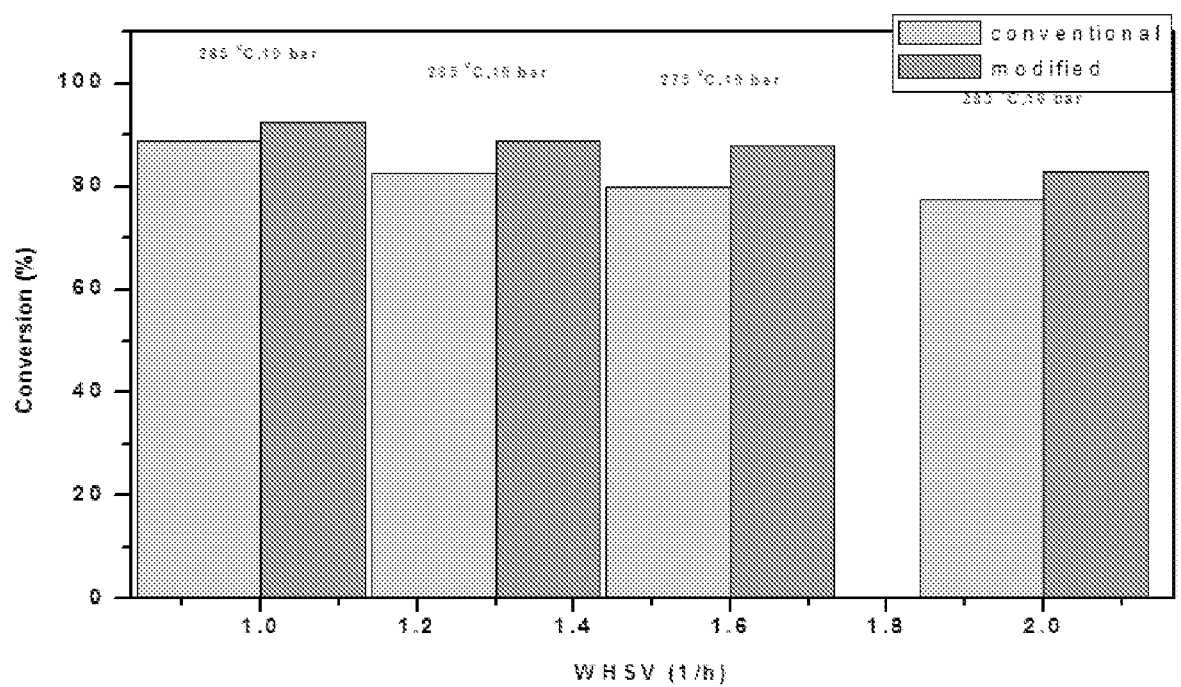
FIG. 5 shows the comparison plot performance of conical reactor with conventional reactor

The comparison plot performance of the conical reactor with a conventional reactor is depicted by FIG. 5. Conversion plots show that the newly designed reactor is giving increased conversion compared with the conventional reactor at various WHSV which justifies the better performance of conical rector over the conventional reactor.

Figure 6:
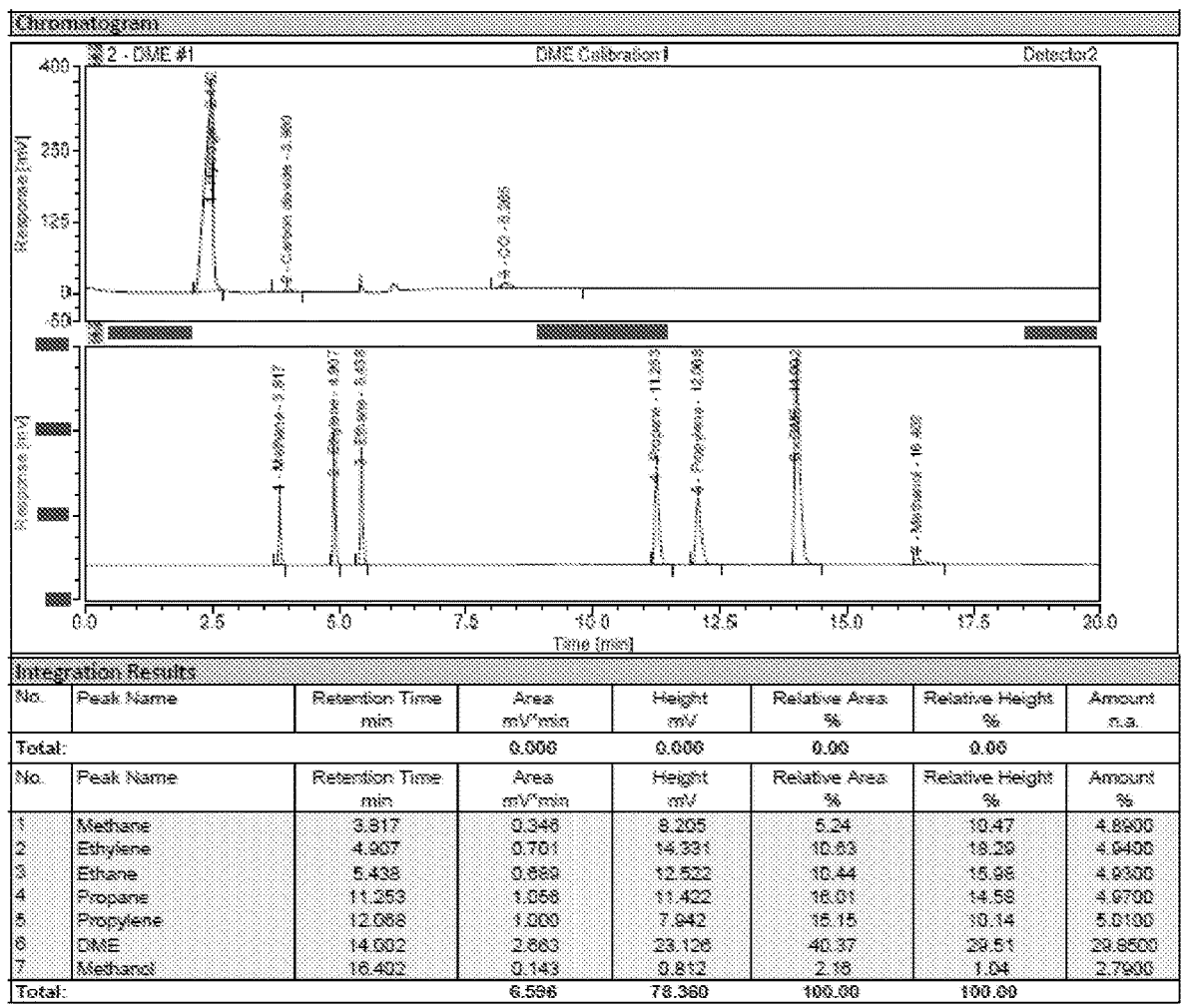
FIG. 6 shows the actual injection of the calibration gas mixture to GC.

FIG. 6 shows the actual injection of the calibration gas mixture to GC. The actual injection of the calibration gas mixture shows the same known composition after analysed with GC and chromeleon 7 software.

Figure 7:
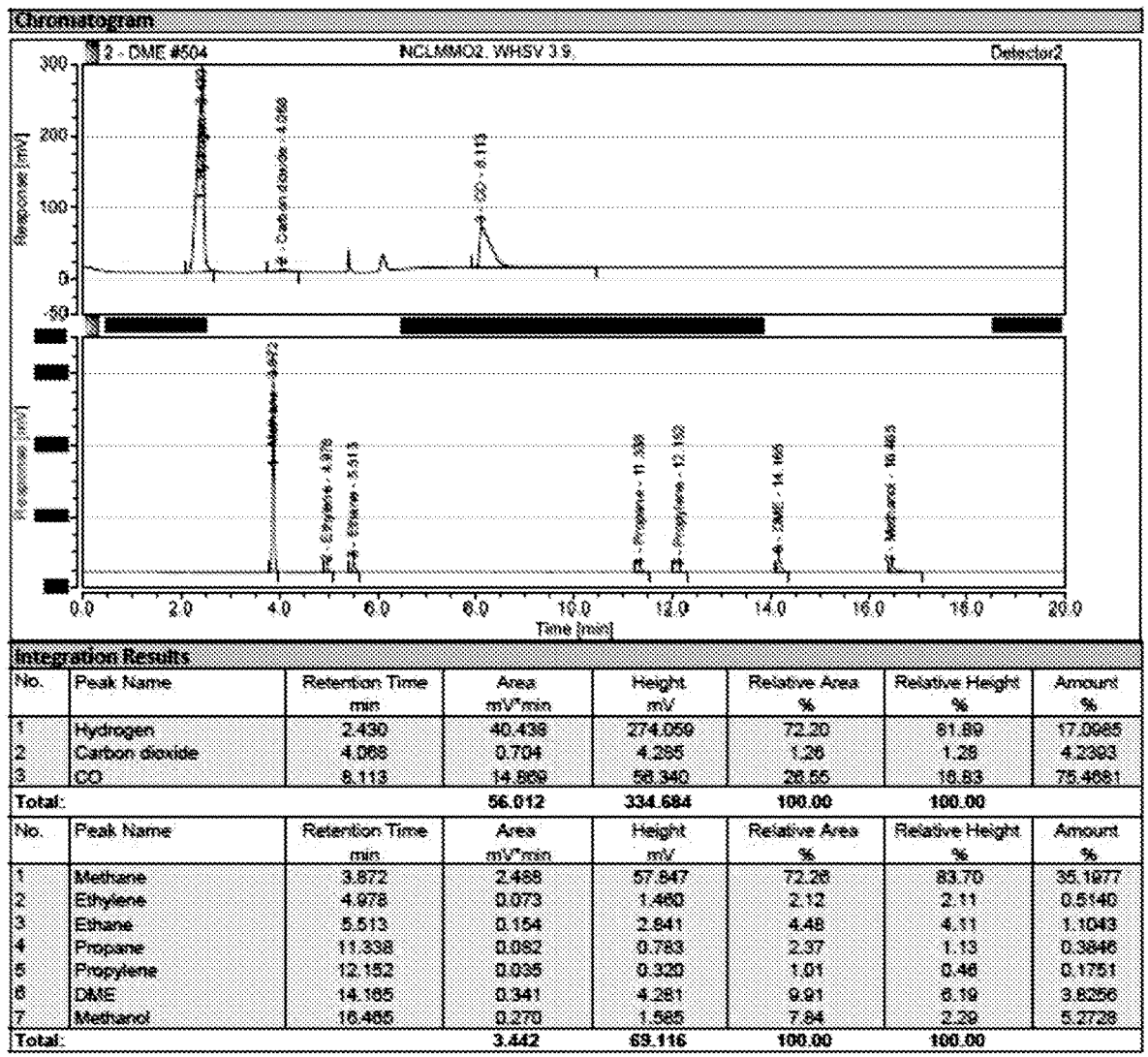
FIG. 7 depicts the actual injection of the reactor out the gas mixture to GC for the confirmation of olefins.

FIG. 7 depicts the actual injection of the reactor out the gas mixture to GC for the confirmation of olefins. Actual injection of reactor outlet gas conforms to the formation of olefins (C2, C3) with this catalyst at 400-450° C. under atmospheric pressure selectivity of the catalyst toward olefins can be further improved by tuning the catalyst composition and reaction conditions.

Figure 8:
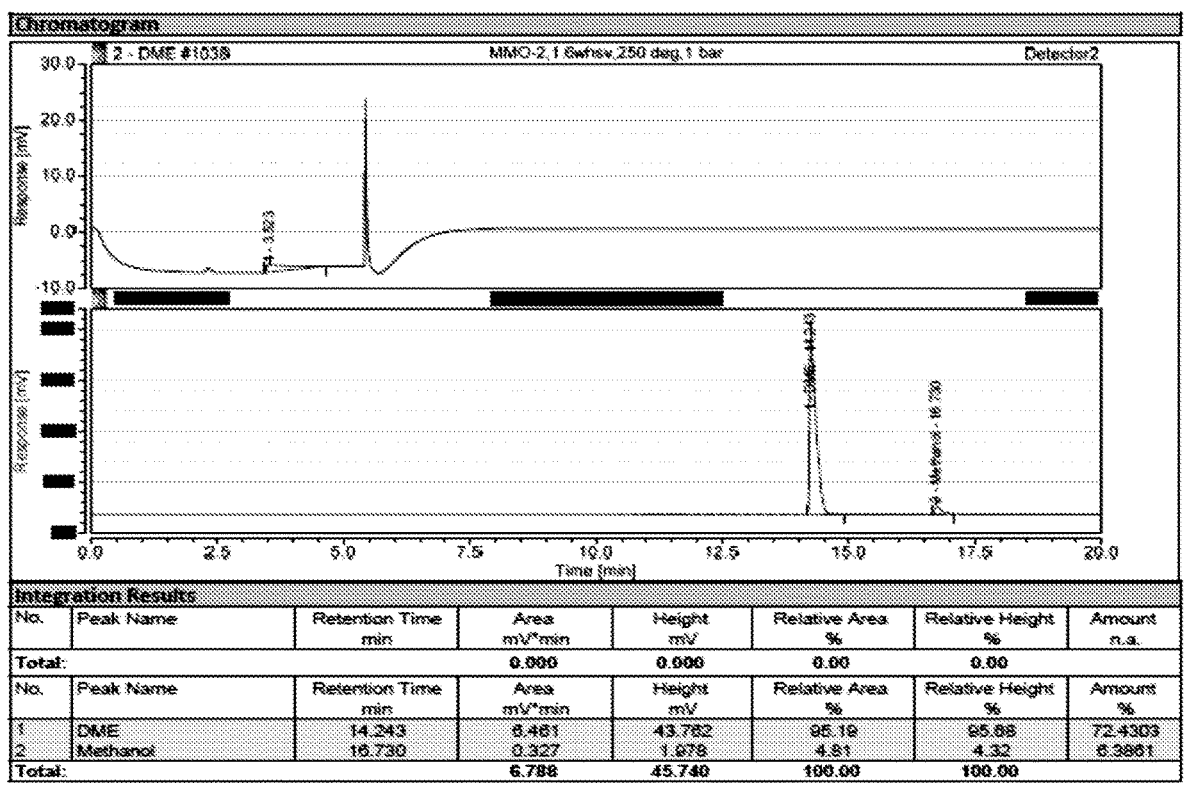
FIG. 8 depicts the actual Injection of reactor gas outlet mixture to GC for the confirmation of DME formation and selectivity.
Figure 9:
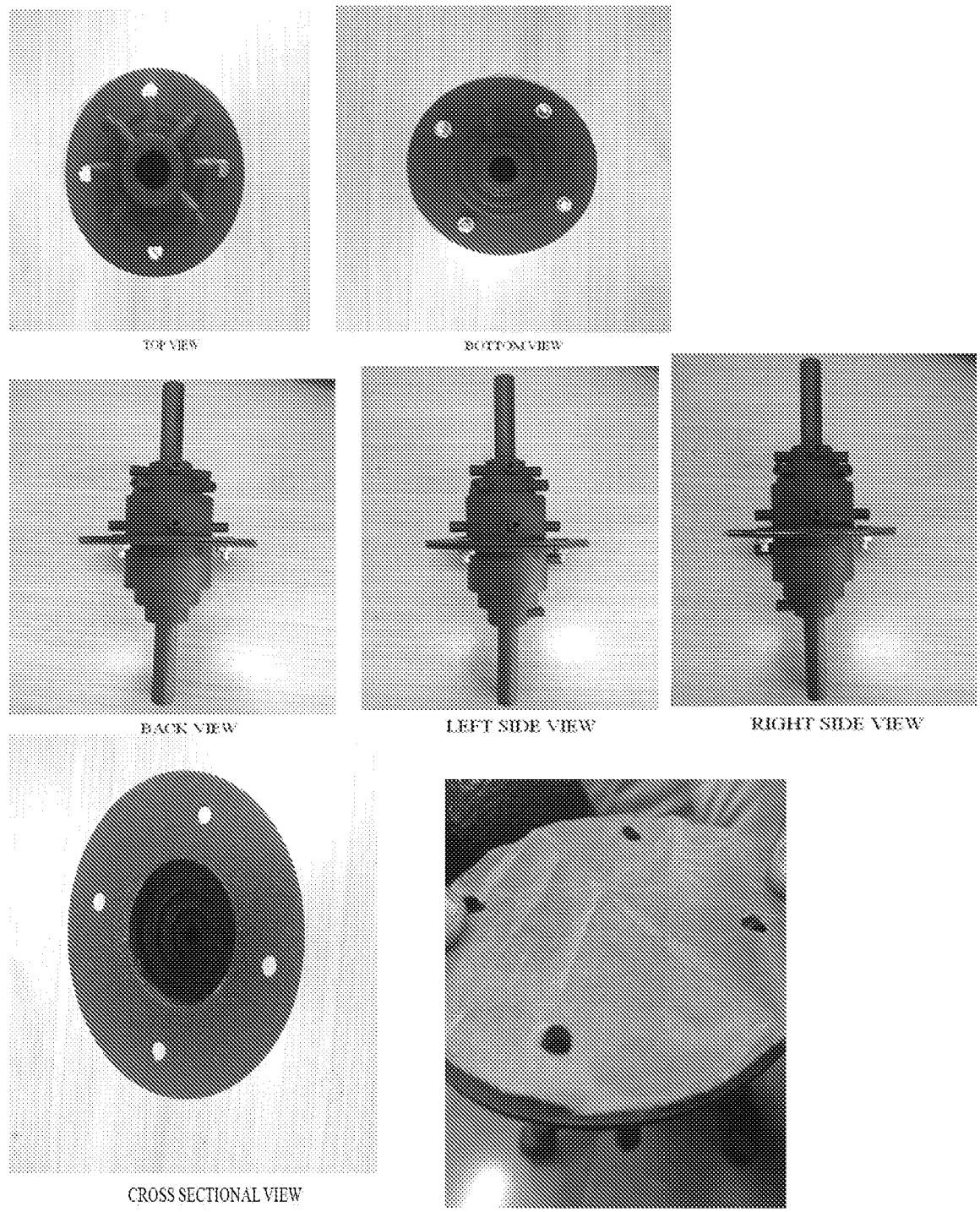
FIG. 9 shows different views of the step conical reactor.

FIG. 8 depicts the actual injection of reactor outlet gas conforms to the formation of DME and no other by-products are observed which shows 100% selectivity towards DME with this catalyst at 260-265° C. under atmospheric pressure.

GENERAL INFORMATION

The pressure of the system is adjusted by imparting a back pressure regulator. The reactor furnace is having surface heating zones and their temperatures are set by an electric jacket equipped with a PID (Proportional, Integral, and derivative) controller to the predetermined temperature with the accuracy of ±0.5° C. Argon is used as a carrier gas to provide the required pressure and for creating the desired methanol partial pressure. The flow rate of Argon gas is controlled by a mass flow controller. Liquid methanol, which consequently evaporated in the pre-heater zone of the furnace and is mixed in gaseous state with Argon, is injected into the system by a dozing pump. The reactor output stream, after passing through a double pipe heat exchanger, enters a two-phase separator.

The output gas from the reactor is analysed every 60 min to 180 min by an on-line gas chromatograph using a TCD detector, a 0.53 mm×30 m HP-Plot Q capillary column, and Argon as the carrier gas, as well as condensed methanol-water liquid samples are also analysed using HPLC. To have a better understanding of the catalyst performance, the gas sample is injected to on-line gas chromatography and obtained data plots are analysed using chromeleon 7 software in which calibration gas mixture of the following composition is already injected.

| Gas | PPM | Vol % |
| --- | --- | --- |
| CO | 3.52352 | 10.4 |
| Methanol | 1.080288 | 2.79 |
| Hydrogen | 0.662596 | 27.38 |
| DME | 16.639793 | 29.85 |
| $CO_2$ | 2.550196 | 4.79 |
| Methane | 0.946704 | 4.89 |
| Ethane | 1.78959 | 4.93 |
| Ethylene | 1.673672 | 4.94 |
| Propane | 2.646028 | 4.97 |
| Propylene | 2.546082 | 5.01 |

EXAMPLES

The following examples are given by way of illustration and therefore should not be construed to limit the scope of the invention.

Example 1: Synthesis of Dimethyl Ether in a Conical Reactor 150 g of synthesized catalyst samples were loaded into the fix bed conical reactor and 100 g catalyst is loaded in polishing reactor unit. At first, the catalyst was activated in the presence of nitrogen and Oxygen with a 50 cm$^3$ min$^{-1}$ flow rate, at the temperature of 350 to 650° C. with a ramp rate of 3° C./min for 12 hrs. The catalyst bed was then cooled to 260° C. then nitrogen and airflow were stopped. After stabilization of temperature, liquid methanol at a flow rate of 8.5 ml·min$^1$ was injected into the reactor and carrier gas flow was stopped. Out of which 1 ml/min methanol injected as reflux in the reactive distillation column. The methanol partial pressure and WHSV in the reactor were 1 atm and 0.5 h$^{-1}$, respectively. The reaction temperature was set at 260° C. under 10 bar pressure for selective DME synthesis. The conversion is 88% and selectivity of DME 99.3% Example 2: Synthesis of dimethyl ether in a conical reactor 150 g of synthesized catalyst samples were loaded into the fix bed conical reactor and 100 g catalyst is loaded in polishing reactor unit. At first, the catalyst was activated in the presence of nitrogen and Oxygen with a 50 cm$^3$ min$^{-1}$ flow rate, at the temperature of 350 to 650° C. with a ramp rate of 3° C./min for 12 hrs. The catalyst bed was then cooled to 260° C. then nitrogen and airflow were stopped. After stabilization of temperature, liquid methanol at a flow rate of 8.5 ml·min$^1$ was injected into the reactor and carrier gas flow was stopped. Out of which 1 ml/min methanol injected as reflux in the reactive distillation column. The methanol partial pressure and WHSV in the reactor were 1 atm and 1.6 h$^{-1}$, respectively. The reaction temperature was set at 260° C. under 10 bar pressure for selective DME synthesis. The conversion is 85% and selectivity of DME is 99.8%.

The reaction temperature can be increased to 450° C. under atmospheric pressure for olefins synthesis.

The pressure of the system was adjusted by imparting a back pressure regulator. The reactor furnace was having surface heating zones and their temperatures were set by an electric jacket equipped with a PID controller to the predetermined temperature with the accuracy of ±0.5° C. Argon was used as a carrier gas to provide the required pressure and for creating the desired methanol partial pressure. The flow rate of Argon gas was controlled by a mass flow controller. Liquid methanol, which consequently evaporated in the pre-heater zone of the furnace and was mixed in gaseous state with Argon, was injected into the system by a dozing pump. The reactor output stream, after passing through a double pipe heat exchanger, entered a two-phase separator.

Example 3: Synthesis of Diethyl Ether in a Conical Reactor 150 g of synthesized catalyst samples were loaded into the fix bed conical reactor and 100 g catalyst is loaded in polishing reactor unit. At first, the catalyst was activated in the presence of nitrogen and Oxygen with a 50-500 cm$^3$ min$^{-1}$ flow rate, at the temperature of 350 to 650° C. with a ramp rate of 3° C./min for 12 hrs. The catalyst bed was then cooled to 275° C. then nitrogen and airflow were stopped. After stabilization of temperature, liquid ethanol at a flow rate of 8.5 ml·min$^1$ was injected into the reactor and carrier gas flow was stopped Out of which 1 ml/min ethanol injected as reflux in the reactive distillation column. The ethanol partial pressure and WHSV in the reactor were 1 atm and 0.5 h$^{-1}$, respectively. The reaction temperature was set at 275° C. under 1 bar pressure for selective DEE synthesis. The conversion is 84% with selectivity of DEE is 93%.

Example 4: Synthesis of Diethyl Ether in a Conical Reactor 150 g of synthesized catalyst samples were loaded into the fix bed conical reactor and 100 g catalyst is loaded in polishing reactor unit. At first, the catalyst was activated in the presence of nitrogen and Oxygen with a 50-500 cm$^3$ min$^{-1}$ flow rate, at the temperature of 350 to 650° C. with a ramp rate of 3° C./min for 12 hrs. The catalyst bed was then cooled to 275° C. then nitrogen and airflow were stopped. After stabilization of temperature, liquid ethanol at a flow rate of 8.5 ml·min$^1$ was injected into the reactor and carrier gas flow was stopped Out of which 1 ml/min ethanol injected as reflux in the reactive distillation column. The ethanol partial pressure and WHSV in the reactor were 1 atm and 1.6 h$^{-1}$, respectively. The reaction temperature was set at 275° C. under 1 bar pressure for selective DEE synthesis. The conversion is 75% and selectivity of DEE is 96.0%.

Example 5

Two-Phase Separator: Separation of Liquid and Gas in a Separator

The Outlet from the fixed bed reactor was further sent to the phase separator where methanol and water were condensed under the pressure of 10 bar and at 120° C. Dimethyl ether/di ethyl ether came out through Back Pressure Regulator (BPR) as is a non-condensable gas. The condensed mixture of methanol/ethanol and water formed a liquid level at the bottom of the separator. The bottom temperature of the separator was maintained at 120° C. to maintain the dimethyl/di ethyl ether ether in the vapour phase.

Distillation Coupled with Polishing Reactor Unit

The condensed methanol/ethanol and water mixture formed a liquid level in a U loop that connected phase separator to the distillation coupled polishing reactor where the bottom temperature was maintained at 150-170° C. so methanol/ethanol would vaporize there. The vapour phase methanol/ethanol further reacted in the catalyst zone to give dimethyl/di ethyl ether at 260° C. and 10 bar pressure. Part of the condensed mixture of methanol/etahnol and water or fresh methanol/etahnol can be used as reflux to ensure the purity of methanol/ethanol vapour reaching the polishing catalyst bed.

ADVANTAGES OF THE INVENTION

A new reactor set up increases catalyst activity and durability as the design helps to eliminate the hotspots.
The reactor process gives higher conversion (90-92%) due to a modified design of the reactor setup as the design and arrangement of separation units helps to remove formed products
The modified design of the reactor and process gives 100% selectivity of dimethyl ether with no by-products.
Reaction throughput is increased by 30% compared to a conventional reactor process. as more catalyst surface area is interacting with fresh reactants, step conical design offers optimum superficial velocity for the reactants and products through the catalyst bed.
In-situ continuous product separation can save the cost of—post-processing of the product.

We claim:

1. An intensified process for preparation of dialkyl ether comprising:
    dehydrating an alcohol in a reactor system, wherein the reactor system comprises a step conical fixed bed reactor coupled with a polishing reactive distillation unit, by injecting a liquid alcohol, at a flow rate of 2.65-8.5 ml·min$^{-1}$ and WHSV of 0.5-1.61 h$^{-1}$ at a temperature in a range of 200-260° C. under 1-10 bar pressure at the reactor system to obtain dialkyl ether, wherein the process is catalyst independent and wherein the step conical fixed bed reactor is divided into an upper section and a lower section by a perforated screen, wherein the perforated screen is configured for supporting a catalyst and wherein the upper section and the lower section have varying steps diameter adapted to provide a surface area for contact of the catalyst for a fresh incoming feed.

2. The process as claimed in claim 1, wherein said dialkyl ether is dimethyl or diethyl ether.

3. A reactor system for preparation of dialkyl ether, the reactor system comprising:
    a step conical fixed bed reactor divided into an upper section and a lower section by a perforated screen, wherein the perforated screen is configured for supporting a catalyst and wherein the upper section and the lower section have varying steps diameter adapted to provide a surface area for contact of the catalyst with a fresh incoming feed;
    a phase separator connected to the step conical fixed bed reactor through a heat exchanger, wherein the phase separator is configured to remove an output stream of an unreacted reactant and a by-product by keeping a temperature of 120° C. at a bottom of the phase separator using the heat exchanger, wherein the unreacted reactant comprises an alcohol and the by-product comprises water;
    a reactive distillation column adapted to distill the unreacted reactant and the by-product to separate the unreacted reactant as a vapour;
    a reflux inlet adapted to further purify the unreacted reactant by refluxing a fresh alcohol; and
    a polishing catalyst zone adapted to react with a vapour phase of the alcohol from the reactive distillation column to form dialkyle ether and water.

4. The reactor system as claimed in claim 3, wherein the step conical fixed bed reactor is provided with a back pressure regulator to adjust the back pressure.

5. The reactor system as claimed in claim 3, wherein the step conical fixed bed reactor comprises multiple inlets adapted for letting in a plurality of reactants into the step conical fixed bed reactor.

6. The reactor system as claimed in claim 3, wherein the step conical fixed bed reactor is equipped with an in-situ heat integration and a cooling arrangement comprising a plurality of water inlets and a plurality water outlets adapted to facilitate in situ cooling of a product gas.

7. The reactor system as claimed in claim 3, wherein the perforated screen for catalyst support is adapted to get a back pressure to avoid channeling, wherein the perforated screen for catalyst support has a size in a range of 5-100 micron.

8. The reactor system as claimed in claim 3, wherein the upper section of the step conical fixed bed reactor is equipped with a gradually increasing inner diameter, wherein the inner diameter is increasing per step from 3.3×x cm, 5.3×x cm and 7.3×x cm respectively, and wherein the lower section of step conical fixed bed reactor is equipped with a gradually decreasing inner diameter wherein the inner diameter is decreasing per step from 7.3×x cm, 5.3×x cm and 3.3×x cm respectively wherein x is a scaling factor, wherein x depends on an amount of catalyst loaded in the step conical fixed bed reactor and, wherein a step conical arrangement of the step conical fixed bed reactor is a step angle in a range of 10-90°.

9. The step conical fixed bed reactor as claimed in claim 3, wherein the step conical fixed bed reactor is configured to gives 30-50% higher reaction throughput when compared to a conventional fixed bed reactor.

10. The reactor system as claimed in claim 3, wherein the reactive distillation column comprises a reboiler adapted for further distillation of the unreacted reactants and by-product.

11. The reactor system as claimed in claim 3, wherein the alcohol comprises methanol or ethanol.

12. The reactor system as claimed in claim 3, wherein the dialkyle ether is dimethyl ether or diethyl ether.

* * * * *